US008110387B2

(12) United States Patent
Hahnhägerdal et al.

(10) Patent No.: US 8,110,387 B2
(45) Date of Patent: Feb. 7, 2012

(54) POLYPEPTIDE HAVING NADH DEPENDENT HMF REDUCTASE ACTIVITY

(75) Inventors: Bärbel Hahnhägerdal, Lund (SE); Gunnar Lidén, Lund (SE); Tobias Modig, Kävlinge (SE); João Almeida, Taguatinga DF (BR); Boaz Laadan, Even-Yehuda (IL); Marie F. Gorwa-Grauslund, Klagshamn (SE)

(73) Assignee: C5 Ligno Technologies Lund AB, Lund (SE)

( * ) Notice: Subject to any disclaimer, the term of this patent is extended or adjusted under 35 U.S.C. 154(b) by 36 days.

(21) Appl. No.: 12/671,241

(22) PCT Filed: Jul. 11, 2008

(86) PCT No.: PCT/SE2008/000444
§ 371 (c)(1),
(2), (4) Date: Jun. 23, 2010

(87) PCT Pub. No.: WO2009/017441
PCT Pub. Date: Feb. 5, 2009

(65) Prior Publication Data
US 2010/0267111 A1 Oct. 21, 2010

(30) Foreign Application Priority Data

Jul. 31, 2007 (SE) ...................................... 0701797

(51) Int. Cl.
C12N 9/02 (2006.01)
C12N 15/00 (2006.01)
C12N 1/20 (2006.01)
C07H 21/02 (2006.01)

(52) U.S. Cl. ... 435/189; 435/6.1; 435/252.3; 435/320.1; 536/23.2

(58) Field of Classification Search .................. 435/189, 435/6.1, 252.3, 320.1; 536/23.2
See application file for complete search history.

(56) References Cited

FOREIGN PATENT DOCUMENTS
WO    WO 03/072602      9/2003
WO    WO 2005/111214   11/2005

OTHER PUBLICATIONS

Almieda et al. "Mini-Review: Increased tolerance and conversion of inhibitors in lignocellulosic hydrolysates by *Saccharomyces cerevisiae*." *J. of Clinical Technology and Biotechnology*. vol. 82. 2007. pp. 340-349.
Database AX829451, updated May 2006.
Database AX829452, updated Dec. 2003.
Bitter et al. "Expression of heterologous genes in *Saccharomyces cerevisiae* from vectors utilizing the glyceralde-hyde-3-phosphate dehydrogenase gene promoter." *Gene*. vol. 32. 1984. pp. 263-274.
Brandberg et al. "Continuous Fermentation of Undetoxified Dilute Acid Lignocellulose Hydrolysate by *Saccharamoyces cerevisiae* ATCC 96581 Using Cell Recirculation." *Biotechnol. Prog.* vol. 21. 2005. pp. 1093-1101.
EPOP AX829451, Dec. 12, 2003.
Gray et al. "Bioethanol." *Current Opinion in Chem. Biology*. vol. 10. 2006. pp. 141-146.
Hahn-Hagerdal et al. "Bio-ethanol—the fuel of tomorrow from the residues of today." *TRENDS*. vol. 10. No. 2. 2006. pp. 141-146.
Larroy et al. "Characterization of the *Saccharomyces cerevisiae* YMR318C (ADH6) gene product as a broad specificity NADPH-dependent alcohol dhydrogenase: relevance in aldehyde reduction." *Biochem J*. vol. 361. 2002. pp. 163-172.
Larsson et al. "Development of *Saccharomyces cerevisiae* Strain with Enhanced Resistancec to Phenolic Fermentation Inhibitors in Lignocellulose Hydrolysates by Heterologous Expression of Laccase." *Applied and Environ. Microbiol.* vol. 67. No. 3. 2001. pp. 1163-1170.
Larsson et al. "The generation of fermentation inhibitors during dilute acid hydrolysis of softwood." *Enzyme & Microbiol. Tech*. vol. 24. 1999. pp. 151-159.
Linden et al. "Isolation and Characterization of Acetic Acid-Tolerant Galactose-Fermenting Strains of *Saccharomyces cerevisiae* from a spent sulfite liquor fermentation plant." *Applied & Envrion. Microbiol.* vol. 58. No. 5. 1992. pp. 1661-1669.
Nilsson et al. "Cofactor Dependence in Furan Reduction by *Saccharomyces cerevisiae* in Fermentation of Acid-Hydrolyzed Lignocellulose." *Applied & Envrion. Microbiol.* vol. 71. No. 12. 2005. pp. 7866-7871.
Nilvebrant et al. "Limite for Alkaline Detoxification of Dilute-Acid Lignocellulose Hydrolysates." *Applied Biochem and Biotech*. vol. 105-108. 2003. pp. 615-628.
Petersson et al. "A 5-hydroxymethyl furfural reducing enzyme encoded by the *Saccharomyces cerevisiae* ADH6 gene conveys HMF tolerance." *YEAST*. vol. 23. 2006. pp. 455-464.
Taherzadeh et al. "Physiological effects of 5-hydroxymethylfurfural on *Saccharomyces cerevisiae*." *Appl. Microl. Bioctechnol.* vol. 53. 2000. pp. 701-708.
Verduyn et al. "Effect of Benzoic Acid on Metabolic Fluxes in Yeasts: A Continuous-Culture Study on the Regulation of Respiration and Alcoholic Fermentation." *YEAST*. vol. 8. 1992. pp. 501-517.
Wahlbom et al. "Furfural, 5-Hydroxymethyl Furfural, and acetoin act as external electron acceptors during anaerobic fermentation of Xylose in Recombinant *Saccharomyces cerevisiae*."*Biotechl. and Bioengineering*. vol. 78. No. 2. 2002. pp. 172-178.
Supplementary European Search Report from EP Application No. 08779227.1 dated Oct. 21, 2010. Almieda et al. "Carbon fluxes of xylose-consuming *Saccharomyces cerevisiae* strains are affected differently by NADH and NADPH usage in HMF reduction." *Appl. Microbiol. Biotechnol*. vol. 84. 2009. pp. 751-761.

*Primary Examiner* — Maryam Monshipouri
(74) *Attorney, Agent, or Firm* — Merchant & Gould P.C.

(57) ABSTRACT

The invention relates to an isolated polypeptide having NADH dependent HMF reductase activity, wherein said polypeptide shows 80% homology to the amino acid sequence shown in SEQ ID NO:2 and which differs from SEQ ID NO:2 in that at least S117L and Y295 or S110 is substituted, a nucleotide sequence coding for said polypeptide, a vector comprising said polypeptide or nucleotide sequence, host comprising said nucleotide sequence or vector as well as the use of the polypeptide for the reduction of furan or carbonyl compounds in lignocellulosic material or in any furan or carbonyl containing material.

17 Claims, 4 Drawing Sheets

SEQUENCE LISTING

<160> NUMBER OF SEQ ID NOS: 2

<210> SEQ ID NO 1
<211> LENGTH: 1047
<212> TYPE: DNA
<213> ORGANISM: Saccharomyces cerevisiae

<400> SEQUENCE: 1

```
atgtctatcc cagaaactca aaaaggtgtt atcttctacg aatcccacgg taagttggaa      60
tacaaagata ttccagttcc aaagccaaag gccaacgaat gttgatcaa cgttaaatac     120
tctggtgtct gtcacactga cttgcacgct tggcacggtg actggccatt gccaactaag     180
ttaccattag ctggtgggca cgaaggtgcc ggtgtcgttg tcggcatggg tgaaaacgtt     240
aagggctgga gatcggtga ctacgccggt atcaaatggt tgaacggttc ttgtatggcc      300
tgtgaatact gtgaattggg taacgaatcc aactgtcctc acgctgactc ctctggttac     360
acccacgacg ttctttcca acaatacgct accgctgacg ctgttcaagc cgctcacatt     420
cctcaaggta ctgacttggc tgaagtcgcc ccagtcttgt gtgctggtat caccgtctac     480
aaggctttga gtctgctaa cttgatggcc ggtcactggg ttgctatctc cggtgctgct     540
ggtggtctag gttctttggc tgttcaatac gccaaggcta tgggttacag agtcttgggt     600
attgacggtg gtgaaggtaa ggaagaatta ttcagatcca tcggtggtga agtcttcatt     660
gacttcacta aggaaaagga cattgtcggt gctgttctaa aggccactga cggtggtgct     720
cacggtgtca tcaacgtttc tgtttccgaa gccgctattg aagcttctac cagatacgtt     780
agagctaacg gtaccaccgt tttggtcggt atgccagctg gtgccaagtg ttgttctgat     840
gtcttcaacc aagtcgtcaa gtccatctcc attgttggtt cttacgtcgg taacagagct     900
gacaccagag aagctttgga cttcttcgcc agaggtttgg tcaagtctcc aatcaaggtt     960
gtcggcttgt ctaccttgcc agaaatttac gaaaagatgg aaaagggtca atcgttggt      1020
agatacgttg ttgacacttc taaataa                                        1047
```

<210> SEQ ID NO 2
<211> LENGTH: 348
<212> TYPE: PRT
<213> ORGANISM: Saccharomyces cerevisiae

<400> SEQUENCE: 2

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Thr Lys Leu Pro Leu Ala
        50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Ser Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Glu Val Ala Pro Val Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

POLYPEPTIDE HAVING NADH DEPENDENT HMF REDUCTASE ACTIVITY

This application is a National Stage Application of PCT/SE2008/000444, filed 11 Jul. 2008, which claims benefit of Ser. No. 0701797-3, filed 31 Jul. 2007 in Sweden and which applications are incorporated herein by reference. To the extent appropriate, a claim of priority is made to each of the above disclosed applications.

FIELD OF INVENTION

The invention relates to an isolated polypeptide having NADH dependent HMF reductase activity, wherein said polypeptide shows 80% homology to the amino acid sequence shown in SEQ ID NO:2 and which differs from SEQ ID NO:2 in that at least S117L and Y295 or S110 are substituted, a nucleotide sequence coding for said polypeptide, a vector comprising said polypeptide or nucleotide sequence, host comprising said nucleotide sequence or vector as well as the use of the polypeptide for the reduction of furan or carbonyl compounds in lignocellulosic material or in any furan or carbonyl containing material.

BACKGROUND OF INVENTION

Bioethanol production from renewable feedstock by baker's yeast *Saccharomyces cerevisiae* has become an attractive alternative to fossil fuels. However, the availability of starch or sucrose based feedstock such as corn grain or sugar cane is expected to be insufficient to cover future worldwide needs for bioethanol (Gray et al., 2006. Bioethanol. Current Opinion Chemical Biology. 10(2):141-146). A foreseen solution is the utilization of lignocellulosic feedstocks, such as corn stover, wheat straw, sugar cane bagasse, wood, etc (Hahn-Hägerdal et al., 2006. Bioethanol—the fuel of tomorrow from the residues of today. Trends Biotechnol. 24(12):549-556). This requires overcoming new challenges associated with the utilization of these complex raw materials.

One of these challenges concerns the presence of inhibitory compounds such as small aliphatic low molecular weight acids, furan derivatives, carbonyl compounds and phenolics that are released during the pretreatment and hydrolysis of lignocellulosic raw materials (Almeida et al., 2007. Increased tolerance of inhibitors in lignocellulosic hydrolysates by *Saccharomyces cerevisiae*. J Chem Technol Biotechnol, 82:340-349). Among these compounds, the presence of the furan derivative 5-hydroxymethylfurfural (HMF), that originates from the dehydration of hexoses, has been reported to result in reduced ethanol productivity during the fermentation of lignocellulosic hydrolysates by *S. cerevisiae* (Taherzadeh et al. 2000. Physiological effects of 5-hydroxymethyl furfural on *Saccharomyces cerevisiae*. Appl Microbiol Biotechnol. 53(6):701-708.). When compared in equimolar amounts with furfural, another inhibitory furan derivative found in hydrolysates, both the volumetric ethanol productivity and the sugar consumption rate by the cells are lower with HMF (Larsson et al., 1999. The generation of fermentation inhibitors during dilute acid hydrolysis of softwood. Enzyme Microbial Technology 24:151-159.). Therefore, either removing HMF and/or improving cellular HMF detoxification are crucial for an industrial fermentation process based on lignocellulosic feedstocks.

WO03072602 discloses a polypeptide having Serin in position 295. However, the polypeptide lacks a leucine in position 117.

Nilsson et al., Applied and Environmetal Microbiology, December 2005, vol 71, page 7866-7871 disclosed that cell extracts from an lignocellulose hydrolysaste tolerant strain TMB3000 displayed a previously unknown NADH-dependent HMF reducing activity, which was not present in the less tolerant strain CBS 8066.

An absolute requirement for the development of fermentation processes based on lignocellulosic feedstocks is the development and optimisation of micro-organisms which are tolerant against the inhibiting compounds mentioned above or strain that can utilise/degrade the inhibiting compounds. *S. cerevisiae* strains have been shown to reduce HMF and furfural (Larsson et al., 1999. The generation of fermentation inhibitors during dilute acid hydrolysis of softwood. Enzyme Microbial Technology 24:151-159) to 2,5-dimethanol (2,5-bis-hydroxymethylfuran) and 2-furanmethanol respectively, however the reduction rate is low and strain dependent. Strain TMB3000 (Lindén et al., 1992. Isolation and characterization of acetic acid-tolerant galactose-fermenting strains of *Saccharomyces cerevisiae* from a spent sulfite liquor fermentation plant. Applied Environmental Microbiology. 58(5):1661-1669) appears to be, so far, the most tolerant strain that can grow in undiluted wood hydrolysates (Brandberg et al., 2005. Continuous fermentation of undetoxified dilute acid lignocellulose hydrolysate by *Saccharomyces cerevisiae* ATCC 96581 using cell recirculation. Biotechnology progress, 21(4):1093-1101).

SUMMARY OF THE INVENTION

The invention relates to the isolation of a new polypeptide having NADH dependent HMF reductase activity, wherein said polypeptide has the ability to reduce a number of compounds. One example of a polypeptide includes a mutated alcohol dehydrogenase (ADH1) from *Saccharomyces cerevisiae*, which in the native form cannot reduce HMF which when mutated can reduce HMF. The invented polypeptide may be used in several processes for the production of bulk and platform chemicals from lignocellulosic material, such as lignocellulosic feedstock, wherein there is a need to detoxify HMF or other furans or derivatives thereof or carbonyl compounds. Examples of biofuels, bulk and platform chemicals include ethanol, butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone, fatty acids, fatty-derived molecules, isoprenoids, isoprenoid-derived molecules, alkanes, isopentanol, isoamylacetate. When using the new polypeptide, increased specific productivity (gram product per gram cell and hour) will be achieved due to the faster removal of inhibitory furan compounds and carbonyl compounds from the medium.

In a first aspect the invention relates to an isolated polypeptide having NADH dependent HMF reductase activity, wherein said polypeptide shows 80% homology to the amino acid sequence shown in SEQ ID NO:2 and which differs from SEQ ID NO:2 in that at least S117L and Y295 or S110 are substituted. By the introduction of a single substitution into SEQ ID NO:2 and at the same time maintaining L in position an improved polypeptide is obtained which efficiently reduces HMF and furfural.

In a second aspect the invention relates to an isolated polypeptide as defined above, wherein said polypeptide differs from SEQ ID NO:2 in that at least Y295C or Y295S or Y295T or S110P are substituted In a third aspect the invention relates to a nucleotide sequence encoding a polypeptide as defined above.

In a fourth aspect the invention relates to a vector comprising the nucleotide sequence.

In a fifth aspect the invention relates to a host cell comprising the nucleotide sequence or the vector.

In a six aspect the invention relates to the use of the polypeptide having NADH dependent HMF reductase activity, the nucleotide sequence, the vector or the host cell for the production of bulk chemicals from lignocellulosic feedstocks, such as those mentioned above. By the use of the improved polypeptides there is an increased sugar consumption rate and growth rate as well as if the host is used for the production of ethanol there is an increased rate of ethanol production by the microorganism compared to when the native polypeptide is used.

By providing a new polypeptide as shown in SEQ ID NO:2 having NADH dependent HMF reductase activity it will for the first time be possible to reduce furan compounds or carbonyl compounds or furan derivatives, such as 5-hydroxymethyl-2-furaldehyde (HMF) using NADH as a co-factor. HMF has been reported to reduce both cell growth and ethanol productivity in baker's yeast, most commonly used for industrial ethanol production. These two problems will now be reduced or eliminated when the new isolated polypeptide is added to the process or the new isolated nucleotide sequence is transferred into a host cell, which is to be used in a process where normally the problem with HMF is present.

DETAILED DESCRIPTION OF THE INVENTION

Definitions

Figure 1:
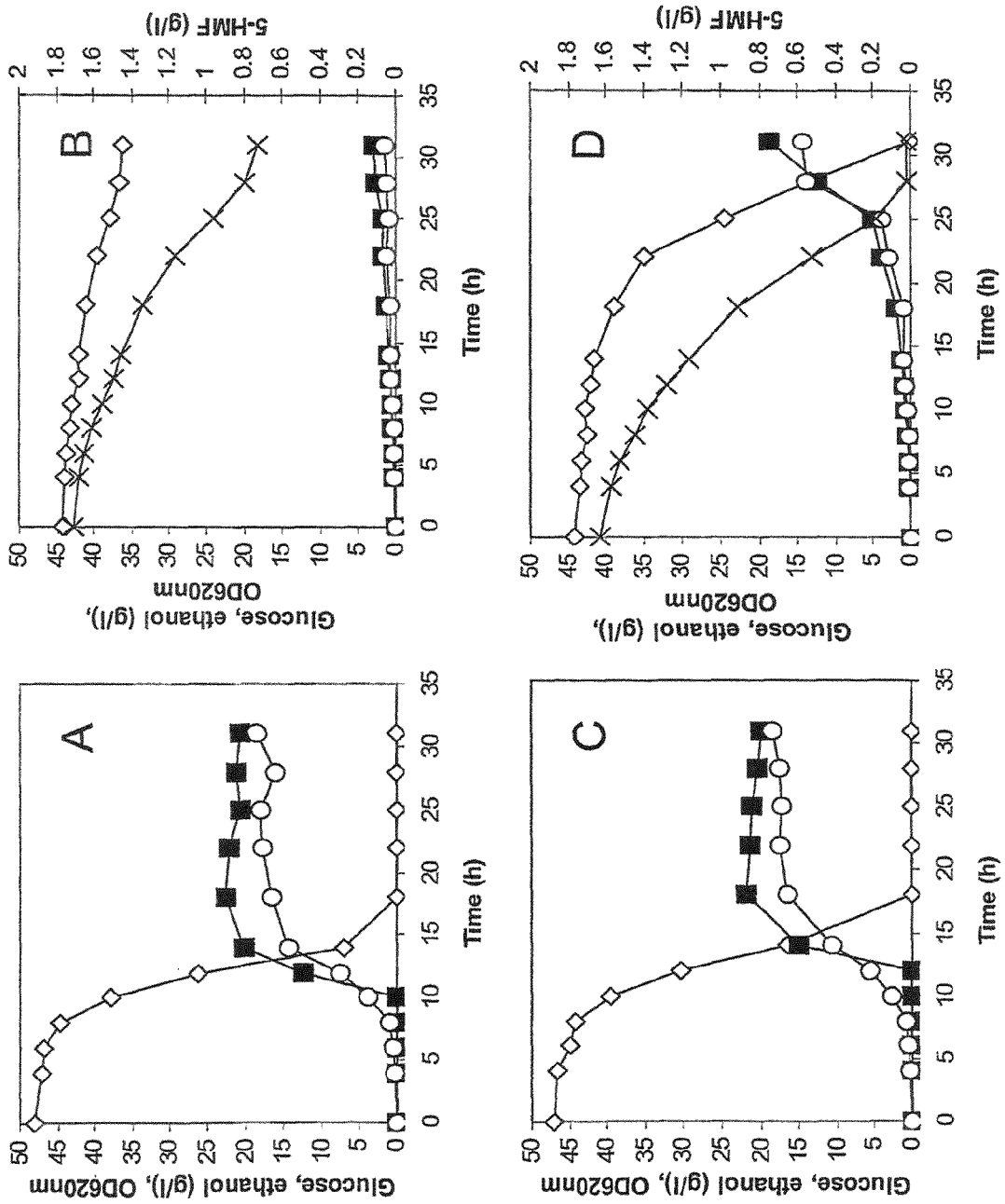
FIG. 1—Substrate and HMF consumption and main product formation in strains TMB3280 (empty plasmid) (A, B) and TMB3206 (mutated ADH1) (C, D) under aerobic conditions. A, C=without HMF addition; B, D=with 20 mM HMF addition. Symbols: ◇ glucose, ○ $OD_{620}$, x HMF, ■ ethanol.

In the context of the present application and invention the following definitions apply:

The term "nucleotide sequence" is intended to mean a consecutive stretch of three or more regions of nucleotide sequences. The nucleotides can be of genomic DNA, cDNA, RNA, semisynthetic or synthetic or a mixture thereof. The term includes single and double stranded forms of DNA or RNA.

The term "analogue thereof" is intended to mean that part of or the entire polypeptide of SEQ ID NO:2 is based on non protein amino acid residues, such as aminoisobutyric acid (Aib), norvaline gamma-aminobutyric acid (Abu) or ornithine. Examples of other non protein amino acid residues can be found at www.hort.purdue.edu/rhodcv/hort640c/polyam/po00008.htm.

The term polypeptide "homology" is understood as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for amino acid sequence comparison are used: GAP creation penalty of 3.0 and GAP extension penalty of 0.1. The relevant part of the amino acid sequence for the homology determination is the mature polypeptide.

The term "vector" as used herein refers to a nucleic acid molecule, either single- or double-stranded, which is isolated from a naturally occurring gene or which is modified to contain segments of nucleic acids in a manner that would not otherwise exist in nature. The term vector is synonymous with the term "expression cassette" when the vector contains the control sequences required for expression of a coding sequence of the present invention. The term vector is also synonymous with the term "integration nucleic acid construct" or "integration fragment" when the construct is to be used to integrate the construct/fragment into the genome of a host.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, polyadenylation sequence, pro-peptide sequence, promoter, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "host cell", as used herein, includes any cell type which is susceptible to transformation, transfection, transduction, and the like with a nucleic acid.

In the present context, amino acid names and atom names are used as defined by the Protein DataBank (PNB) (www.p-db.org), which is based on the IUPAC nomenclature (IUPAC Nomenclature and Symbolism for Amino Acids and Peptides (residue names, atom names etc.), Eur J. Biochem., 138, 9-37 (1984) together with their corrections in Eur J. Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenyl-alanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y), or derivatives thereof.

The terminology used for identifying amino acid positions is illustrated as follows: S110 indicates that the position 110 is occupied by a serine residue in the amino acid sequence shown in SEQ ID NO:2. S110P indicates that the serine residue of position 110 has been substituted with a proline residue.

Polypeptide

The invention relates to a new polypeptide having NADH dependent HMF reductase activity, wherein said polypeptide shows 80% homology to the amino acid sequence shown in SEQ ID NO:2, at least 81, 82, 83, 84, 85, 86, 87, 88, 89, 90, 91, 92, 93, 94, 95, 96, 97, 98, 99% or being the same as SEQ ID NO:2. The invented polypeptide having some unique properties since the enzyme uses NADH as a co-factor for the reduction of HMF and other furan compounds and carbonyl compounds such as those produced during the processing of lignocellulosic material.

Another feature of the isolated polypeptide being that the amino acid residue in position 295 or 110 of SEQ ID NO:2 is substituted. However, that particular amino acid may be altered by for example substitution to another amino acid residue, such as a small uncharged amino acid residue. Examples are Y295C or Y295S or Y295T or S110P.

In addition, the polypeptide shown in SEQ ID NO:2 the amino acid residue S117 should be substituted to L. Substitution of the amino acid residue present in position 295 being important and increases the furfural reductase and substitution of both the amino acid residue present in position 295 and 110 for the production of ethanol.

One example of a polypeptide is shown in SEQ ID NO:2, in which the amino acid residues 295 is C or S, 110 is P. Another specific example is when the amino acid residue 59 is T, 210 is P, 148 is E, 152 is V and 295 is C or S of SEQ ID NO:2. The polypeptide having a new activity, i.e., having NADH dependent HMF reductase activity can therefore be used in a process in which there is a need of detoxifying furan compounds and carbonyl compounds. There will also be an increased specific productivity due to that there will be a faster reduction of the furans and carbonyl compounds, the toxic effects of which slow down the whole process. The polypeptide may be synthetic partly or completely as long as the activity remains.

The polypeptide may also be a hybrid polypeptide. The term "hybrid enzyme" or "hybrid polypeptide" is intended to mean for example those polypeptides of the invention that comprises a first set of amino acid sequences comprising the amino acid residues from about 110 to about 295 as shown in SEQ ID NO:2 fused/linked to a second set of amino acid residues and thereby producing a completely synthetic nucleotide sequence based on the knowledge on suitable amino acid sequences, such as linkers, homologous amino acid sequences etc.

The invented polypeptide was cloned from a yeast strain, *Saccharomyces cerevisiae* TMB3000 (ATCC96581) which was shown to have a unique NADH dependent HMF reductase activity. During the analysis of the polypeptide it was found that the polypeptide was similar to the ADH1 polypeptide, which normally cannot reduce HMF. The sole introduction of a few mutations within the polypeptide altered the activity of the polypeptide and it was surprisingly found that the polypeptide had NADH dependent HMF reductase activity. However, the polypeptide may be obtained from any source or even synthetically made as long as the polypeptide has the properties as the defined polypeptide.

Nucleotide Sequence

Another object of the invention relates the nucleotide sequence shown in SEQ ID NO:1 or by a nucleotide sequence having from at least 60, 65, 70, 80, 81, 82, 83, 84, 85, 86, 87, 88, 89, 90, 91, 92, 93, 94, 95, 96, 97, 98, 99% homology to the nucleotide sequence shown in SEQ ID NO:1 encoding the polypeptide having NADH dependent HMF reductase activity. The nucleotide sequence may be obtained by standard cloning procedures used in genetic engineering to relocate the DNA sequence from its natural location to a different site where it will be reproduced. The cloning procedures may involve excision and isolation of a desired DNA fragment comprising the DNA sequence encoding the polypeptide of interest, insertion of the fragment into a vector molecule, and incorporation of the recombinant vector into a host cell where multiple copies or clones of the DNA sequence will be replicated. An isolated DNA sequence may be manipulated in a variety of ways to provide for expression of the polypeptide of interest. Manipulation of the DNA sequence prior to its insertion into a vector may be desirable or necessary depending on the expression vector. The techniques for modifying DNA sequences utilizing recombinant DNA methods are well known in the art.

The nucleotide sequence to be introduced into the DNA of the host cell may be integrated in vectors comprising the nucleotide sequence operably linked to one or more control sequences that direct the expression of the coding sequence in a suitable host cell under conditions compatible with the control sequences. A nucleotide sequence encoding a polypeptide may be manipulated in a variety of ways to provide for expression of the polypeptide The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including native, mutant, truncated, and hybrid promoters, and may be obtained from genes encoding extracellular or intracellular polypeptides either homologous or heterologous to the host cell. The promoter may be a weak or a strong promoter that is constitutive or regulated in the host to be used.

Examples of suitable promoters for directing the transcription of the nucleic acid constructs in bacteria of the present invention are described in "Useful proteins from recombinant bacteria" in Scientific American, 1980, 242: 74-94; and in Sambrook J et al., 1989 Molecular Cloning. A Laboratory Manuel. Cold Spring Harbor Laboratory Press, Cold Spring Harbor, N.Y., supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters may be obtained for example from the genes for *Saccharomyces cerevisiae* enolase (ENO1), *S. cerevisiae* galactokinase (GAL1), *S. cerevisiae* alcohol dehydrogenase 2 (ADH2), *S. cerevisiae* glyceraldehyde-3-phosphate dehydrogenase (TDH1), *S. cerevisiae* glyceraldehyde-3-phosphate dehydrogenase (TDH3) (Bitter and Egan. Expression of heterologous genes in *Saccharomyces cerevisiae* from vectors utilizing the glyceraldehyde-3-phosphate dehydrogenase gene promoter. (1984) Gene 32: 263-274, *S. cerevisiae* alcohol dehydrogenase 1 (ADH1), *S. cerevisiae* 3-phosphoglycerate kinase (PGK1) or *S. cerevisiae* cytochrome C (CYC1) (Karhumaa et al. Investigation of limiting metabolic steps in the utilization of xylose by recombinant *Saccharomyces cerevisiae* using metabolic engineering. (2005) Yeast 5:359-68). Another example of a yeast promoter is the constitutive truncated HXT7 promoter (Hauf et al. Enzym Microb Technol (2000) 26:688-698). Other suitable vectors and promoters for use in yeast expression are further described in EP A-73,657 to Hitzeman, which is hereby incorporated by reference.

The present invention also relates to vectors as defined above which may comprise a DNA sequence encoding the polypeptide, a promoter, and transcriptional and translational stop signals as well as other DNA sequences. The vector comprises various DNA and control sequences known for a person skilled in the art, which may be joined together to produce a vector which may include one or more convenient restriction sites to allow for insertion or substitution of the DNA sequence encoding the polypeptide at such sites. Alternatively, the DNA sequence of the present invention may be expressed by inserting the DNA sequence or a DNA construct comprising the sequence into an appropriate vector for expression. In creating the vector, the coding sequence is located in the vector so that the coding sequence is operably linked with the appropriate control sequences for expression and possibly secretion.

The vector may be any vector (e.g., a plasmid, virus or an integration vector), which can be conveniently subjected to recombinant DNA procedures and can bring about the expression of the DNA sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, a cosmid or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon. The vector may also be an integration vector comprising solely the gene or part of the gene to be integrated.

The vectors of the present invention preferably contain one or more selectable markers, which permit easy selection of transformed cells. A selectable marker is a gene the product of which provides for biocide or viral resistance, resistance to heavy metals, prototrophy to auxotrophs and the like.

Useful expression vectors for eukaryotic hosts, include, for example, vectors comprising control sequences from SV40, bovine papilloma virus, adenovirus and cytomegalovirus. Specific vectors are, e.g., pcDNA3.1(+)Hyg (Invitrogen, Carlsbad, Calif., U.S.A.) and pCI-neo (Stratagene, La Jolla, Calif., U.S.A.). Useful expression vectors for yeast cells include, for example, the 2μ (micron) plasmid and derivatives thereof, the YIp, YEp and YCp vectors described by Gietz and Sugino (1988, "New yeast vectors constructed with in vitro mutagenized yeast genes lacking six-base pair restriction sites", Gene 74:527-534), the vectors described in Mumberg et al (Mumberg, Muller and Funk, 1995, "Yeast vectors for the controlled expression of heterologous proteins in different genetic backgrounds." Gene 156:419-422), YEplac-HXT vector (Karhumaa et al., 2005. Investigation of limiting metabolic steps in the utilization of xylose by recombinant *Saccharomyces cerevisiae* using metabolic engineering. Yeast. 22(5):359-68)), the POT1 vector (U.S. Pat. No. 4,931,373), the pJSO$_{37}$ vector described in Okkels, Ann. New York Acad. Sci. 782, 202-207, 1996, the pPICZ A, B or C vectors (Invitrogen). Useful vectors for insect cells include pVL941, pBG311 (Cate et al., "Isolation of the Bovine and Human Genes for Mullerian Inhibiting Substance and Expression of the Human Gene in Animal Cells", Cell, 45, pp. 685-98 (1986), pBluebac 4.5 and pMelbac (both available from Invitrogen). Useful expression vectors for bacterial hosts include known bacterial plasmids, such as plasmids from *E. coli*, including pBR322, pET3a and pET12a (both from Novagen Inc., Wis., U.S.A.), wider host range plasmids, such as RP4, phage DNAs, e.g., the numerous derivatives of phage lambda, e.g., NM989, and other DNA phages, such as M13 and filamentous single stranded DNA phages. Examples of suitable viral vectors are Adenoviral vectors, Adeno associated viral vectors, retroviral vectors, lentiviral vectors, herpes vectors and cytomegalo viral vectors.

The vectors of the present invention may contain an element(s) that permits stable integration of the vector into the host cell genome or autonomous replication of the vector in the cell independent of the genome of the cell. The vectors of the present invention may be integrated into the host cell genome when introduced into a host cell. For integration, the vector may rely on the DNA sequence encoding the polypeptide of interest or any other element of the vector for stable integration of the vector into the genome by homologous or non homologous recombination.

Alternatively, the vector may contain additional DNA sequences for directing integration by homologous recombination into the genome of the host cell. The additional DNA sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding DNA sequences. On the other hand, the vector may be integrated into the genome of the host cell by non-homologous recombination. These DNA sequences may be any sequence that is homologous with a target sequence in the genome of the host cell, and, furthermore, may be non-encoding or encoding sequences. More than one copy of a DNA sequence encoding a polypeptide of interest may be inserted into the host cell to amplify expression of the DNA sequence.

An Isolated Host Cell

The invention also relates to an isolated host cell, which comprises the nucleotide sequence as defined above either in a vector, such as an expression vector or alternatively has the nucleotide sequence integrated into the genome, e.g. by homologous or heterologous recombination. The nucleotide sequence may be present as a single copy or multiple copies.

The host cell may be any appropriate prokaryotic or eukaryotic cell, e.g., a bacterial cell, a filamentous fungus cell, a yeast, a plant cell or a mammalian cell. Any suitable host cell may be used for the maintenance and production of the vector of the invention, such as an eukaryotic or prokaryotic cell, for example bacteria, fungi (including yeast), plant, insect, mammal, or other appropriate animal cells or cell lines, as well as transgenic animals or plants. The host cell may be a host cell belonging to a GMP (Good Manufacturing Practice) certified cell-line, such as a mammalian cell-line.

Examples of bacterial host cells include *Escherichia coli*, *Zymomonas* sp. and *Klebsiella* sp.

Examples of suitable filamentous fungal host cells include *Aspergillus* sp., e.g. *A. oryzae*, *A. niger*, or *A. nidulans*, *Fusarium* sp. or *Hypocrea* (formerly *Trichoderma*) sp.

Examples of suitable yeast host cells include *Saccharomyces* sp., e.g. *S. cerevisiae*, *S. bayanus* or *S. carlsbergensis*, *Schizosaccharomyces* sp. such as *Sch. pombe*, *Kluyveromyces* sp. such as *K. lactis*, *Pichia* sp. such as *P. stipitis*, *P. pastoris* or *P. methanolica*, *Hansenula* sp., such as *H. polymorpha*, *Candida* sp., such as *C. shehatae* or *Yarrowia* sp. Examples of *S. cerevisiae* strains are DBY746, AH22, S150-2B, GPY55-15Bα, CEN.PK, USM21, TMB3500, TMB 3400, VTT-A-63015, VTT-A-85068, VTT-c-79093) and their derivatives as well as *Saccharomyces* sp. 1400, 424A (LNH-ST), 259A (LNH-ST) and derivatives thereof.

Examples of suitable insect host cells include a Lepidoptora cell line, such as *Spodoptera frugiperda* (Sf9 or Sf21) or Trichoplusioani cells (High Five) (U.S. Pat. No. 5,077,214).

Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture.

The invented polypeptide, nucleotide sequence, vector or host cell may be used in the production of biofuels, bulk and platform chemicals, such as include ethanol, butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone, fatty acids, fatty-derived molecules, isoprenoids, isoprenoid-derived molecules, alkanes, isopentanol, isoamylacetate. The process concept for the conversion of lignocellulosic feedstock to a bulk chemical such as ethanol may include steps such as a pre-treatment or fractionation step in which the chopped raw material is exposed to neutral, acidic or alkaline pH, at high temperature with or without air/oxygen added, so that the hemicellulose fraction is partially hydrolysed to monomeric and oligomeric sugars, rendering the cellulose fraction susceptible for hydrolysis or in which the chopped raw material is exposed to an organic solvent such as acetone, ethanol or similar, at high temperature, so that the lignin fraction is dissolved and extracted rendering the cellulose and hemicellulose fraction susceptible to hydrolysis. The hydrolysis of the pretreated and fractionated material may be performed with concentrated or diluted acids or with cellulolytic and hemicellulolytic enzyme mixtures.

Following examples are intended to illustrate, but not to limit, the invention in any manner, shape, or form, either explicitly or implicitly.

EXAMPLES

Example 1

Identification of NADH-dependent HMF Reductase

Purification of NADH-dependent HMF Reductase

The industrial strain TMB3000 (ATCC96581) (Lindén et al., 1992, Isolation and characterization of acetic acid-tolerant galactose-fermenting strains of *Saccharomyces cerevisiae* from a spent sulfite liquor fermentation plant. Applied Environmental Microbiology 58(5):1661-1669) was grown in rich medium containing 10 g/l yeast extract, 20 g/l peptone and 20 g/l glucose supplemented with 10% spruce hydrolysate (Nilvebrant et al., 2003, Limits for alkaline detoxification of dilute-acid lignocellulose hydrolysates. Applied Biochemistry Biotechnology. 105-108:615-628) adjusted to pH 5.5. The hydrolysate was centrifuged for 10 minutes at 5000 g and supernatant was injected through 2μ filter (Sarstedt, Nümbrecht, Germany) before addition to the autoclaved medium. Growth took place in 1 L shake flasks (non-baffled), containing 250 mL medium at 200 rpm and 30° C. Inoculation from a 5 ml over-night pre-culture in rich medium (without hydrolysate) was to OD620 of 0.1, and cells were harvested at OD620 about 4, after 24 hours.

Cells were harvested and washed twice with double distilled water before being re-suspended in Y-PER detergent (Pierce, Rockford, Ill.), 1 ml/0.6 g cells. After gentle shaking at room temperature for 50 minutes the suspension was centrifuged for 20 minutes at 15000 g. Supernatant was collected and used for enzymatic assays and further purification steps. Coomassie protein assay reagent (Pierce, Rockford, Ill.) was used in Bradford assay for the determination of protein concentration according to the manufacturer's recommendations. Measurements of NADH-dependent furan reduction were conducted according to Wahlbom and Hahn-Hägerdal (2002, Furfural, 5-hydroxymethyl furfural, and acetoin act as external electron acceptors during anaerobic fermentation of xylose in recombinant *Saccharomyces cerevisiae*. Biotechnology and Bioengineering. 78(2):172-178) with the following modification: NADH concentration was set to 200 μM. All measurements were performed at 30° C. in a U-2000 spectrophotometer (Hitachi, Tokyo, Japan).

For the identification of the enzyme responsible for NADH-dependent HMF reduction, the protein solution was fractionated using ammonium sulphate precipitation, size exclusion and affinity chromatography according to the following protocol: cell extract (15 mL) was mixed with 10 ml saturated ammonium sulphate solution to a final concentration of 40%. After 1 hour of gentle shaking at 4° C. the mixture was centrifuged at 15000 g for 20 minutes. The pellet was kept on ice for immediate usage or at −20° C. for later usage (named 40% pellet), while the supernatant was mixed with an equal volume that yielded a 70% ammonium sulphate solution. After 3 hours of gentle shaking at 4° C., centrifugation was repeated at 15000 g for 20 minutes. The pellet was again kept on ice or at −20° C. (named 70% pellet), while the supernatant (~40 mL) was dialyzed over-night against 12 l distilled water at 4° C. using Spectra/Por membrane tubing (MWCO 12 kDa-14 kDa) from Spectrum Laboratories, Calif., USA. Size exclusion chromatography was performed using HiLoad 16/60 Superdex 200 column (Amersham Pharmacia Biotech, Uppsala, Sweden). Buffer contained 100 mM Tris-HCl and 0.5M NaCl (pH raised to 6.7 with NaOH), both from Merck, Darmstadt, Germany. Flow rate was adjusted to 1 ml/min using a FPLC system (Amersham Pharmacia Biotech, Uppsala, Sweden) governed by LCC-501 Plus controller. 50 ml of swollen Red Sepharose CL-6B were packed in XK50 column, both from Amersham Pharmacia Biotech, Uppsala, Sweden. Binding buffer contained 20 mM Tris-HCl, pH 6.4, 5 mM $MgCl_2$, 0.4 mM EDTA and 2 µM β-mercaptoethanol. Elution buffer contained in addition 10 mM β-$NAD_+$ (Sigma-Aldrich, St. Louis, Mo., USA). Flow rate was adjusted to 5 ml/min using the FPLC system mentioned above.

Results from the purification steps are presented in Table 1.

TABLE 1

Purification of NADH-dependent HMF reductase from *S. cerevisiae* TMB3000. Purification level is defined as the ratio between the specific activity of a given step and the specific activity at the first step. 1 unit (U) is defined as 1 µmol of NADH oxidized per min at 30° C. and pH 6.7.

| Step | Total protein (mg) | Total activity (units) | Specific activity (mU/mg protein) | Yield (%) | Purification level |
|---|---|---|---|---|---|
| Crude extract | 279 | 65500 | 235 | 100 | 1 |
| Ammonium sulfate precipitation | 145 | 43935 | 303 | 67 | 1.28 |
| Size exclusion chromatography | 2.566 | 2065 | 805 | 3.15 | 3.4 |
| Affinity chromatography | 0.18 | 932 | 5180 | 1.42 | 22 |

Purified fractions were run on SDS-PAGE using Tris-HCl 4%-15% gradient precast gel and Mini-PROTEAN 3 electrophoresis unit, both from Bio-Rad (Hercules, Calif., USA). Precision Plus Protein dual color (Bio-Rad, Hercules, Calif., USA) was used as standard. Gel staining was conducted using 0.25% Coomassie brilliant blue R-250 (ICN Biomedicals, Aurora, Ohio, USA) in a 6:3:1 mixture of $H_2O$:MeOH:HAc. All mass-spectrometry results were obtained from SWE-GENE proteoinics resource centre in Lund, Sweden.

The final purified fraction showed one band on SDS-PAGE corresponding to a molecular mass of 37 kDa. The purified protein was identified as *S. cerevisiae* alcohol dehydrogenase 1 (Adh1) using electrospray ionization mass spectrometry (ESI-MS).

Cloning of ADH1 Gene from *S. cerevisiae* TMB3000

The ADH1 gene from TMB3000 was amplified by PCR from genomic DNA and cloned into YEplac-HXT vector carrying strong constitutive truncated HXT promoter (Hauf et al., 2000. Simultaneous genomic overexpression of seven glycolytic enzymes in the yeast *Saccharomyces cerevisiae*. Enzyme Microb Technol, 26: 688-698) (Karhumaa et al., 2005. Investigation of limiting metabolic steps in the utilization of xylose by recombinant *Saccharomyces cerevisiae* using metabolic engineering. Yeast. 22(5):359-368).

More specifically, genomic DNA of TMB3000 was extracted using Y-DER kit (Pierce, Rockford, Ill.), according to manufacturer's recommendations. PCR for the amplification of the ADH1 gene from TMB3000 was conducted using Pwo DNA polymerase (Roche Diagnostics AB, Bromma, Sweden) with an annealing temperature of 42° C. Two forward and two reverse primers were used in all possible combinations (restriction sites for later cleavage and ligation are underlined): Forward A-5'-GGGC GGATCCATACAATGTCTATCCCAGAAA-3', Forward B-5'-GGGGGGATCCATGTCTATCCCAGAAACTC-3°, Reverse A-5'-CTTT AGATCTTTATTTAGAAGTGTCAACAACG-3', Reverse B-5'-CTTTAGATCTGCTTATTTAGAAGTGTCAACA-3°.

The purified amplicons were mixed and cleaved with BamHI and BglII (Fermentas, Vilnius, Lithuania), then used for ligation with plasmid YEplac-HXT that was previously cleaved with the same restriction enzymes and de-phosphorylated. The ligation product was used to transform *Escherichia coli* DH5α (Life Technologies, Rockville, Md., USA) according to the method of Inoue et al. (1990, High efficiency transformation of *Escherichia coli* with plasmids. Gene 96:23-28). Transformants were selected on Luria-Bertani (LB) agar plates (Ausubel et al., 1995. Current protocols in molecular biology. Wiley, New York) containing ampicillin (50 µg/mL). PCR was performed on several clones in order to verify correct ligation and plasmid was extracted to transform *S. cerevisiae* strain BY4741 ΔADH1 (Invitrogen, Groningen, the Netherlands) using the lithium acetate method (Gietz et al., 1992. Improved method for high efficiency transformation of intact yeast cells. Nucleic Acids Research 20(6):1425). Transformants were selected anaerobically on SD-ura plates (Ausubel et al., 1995. Current protocols in molecular biology. Wiley, New York) containing 20 mM HMF (Sigma-Aldrich, location), 400 µg/ml of Tween 80 and 10 µg/l ergosterol. Plasmid was extracted from clones showing the highest NADH-dependent HMF reductase activity by growing the cells overnight in 5 ml SD medium without uracil, washing with double distilled water and resuspending in 1 ml protoplasting solution (1.2M sorbitol, 100 mM Tris pH7.5, 10 mM $CaCl_2$, 4 U/ml zymolyase, 0.5% β-mercaptoethanol). After 30 minutes shaking at 30° C., cells were harvested and used for plasmid extraction using the QIAprep Spin Miniprep Kit (Qiagen, Hilden, Germany). Plasmid was transformed to *E. coli* and selected on LB plates with 50 µg/ml ampicillin. Colonies were grown in 5 mL LB medium containing ampicilin (50 µg/ml) and used for plasmid extraction using the QIAprep Spin Miniprep Kit (Qiagen, Hilden, Germany). The resulting plasmid was named YEplac-HXT-ADH1-mut.

ADH1 gene from YEPlac-HXT-ADH1-mut was sequenced using the Abi-Prism BigDye cycle sequencing kit (Applied Biosystems, Weiterstadt, Germany). Six mutations resulting in amino acid substitutions (Table 2) were found from the comparison of the sequenced ADH1 gene from TMB3000 with the native ADH1 gene (as reported in SGD, *Saccharomyces* genome database (SGD), www.yeastgenome.org, systematic name YOL086C).

TABLE 2

Comparison of native Adh1 amino acid sequence with predicted sequence of mutated adh1 from TMB3000.

| Position | 59 | 110 | 117 | 148 | 152 | 295 |
|---|---|---|---|---|---|---|
| Native Adh1 | V | S | L | Q | I | Y |
| Adh1 from TMB3000 | T | P | S | E | V | C |

Example 2

In vivo HMF Uptake with Strain Expressing NADH-dependent Reductase

Overexpression in *S. cerevisiae* CEN.PK 113-5D

Plasmid YEplac-HXT-ADH1-mut encoding the mutated ADH1 gene (as described in example 1), as well as the corresponding empty plasmid YEplacHXT (Karhumaa et al., 2005, Investigation of limiting metabolic steps in the utilization of xylose by recombinant *Saccharomyces cerevisiae* using metabolic engineering. Yeast. 22(5):359-368) were used to transform *S. cerevisiae* CEN.PK 113-5D (SUC2, MAL2-8c, MEL, ura3), resulting in strains TMB3206 and TMB3280, respectively. As expected, NADH-dependent HMF reductase activity was only detected in the strain carrying the mutated ADH1 gene (data not shown).

Aerobic in vivo HMF Reduction

Strains TMB3206 and TMB3280 were pre-grown overnight in 5 ml defined medium (Verduyn et al., 1992. Effect of benzoic acid on metabolic fluxes in yeasts: a continuous-culture study on the regulation of respiration and alcoholic fermentation. Yeast, 8, 501-517) at 30° C. and 200 rpm. Cells were used for inoculation to OD620 nm=0.1 in 100 ml defined medium supplemented with 40 g/l glucose in 1 L—baffled shake flasks. Experiments, that were run at 30° C. and 200 rpm, were conducted with and without HMF (2 g/l) added for both strains. Samples were taken every 2 to 4 hours.

Cell concentration was determined from absorbance measurements at 620 nm calibrated against dry-weight measurements from duplicate samples. For dry-weight samples 10 ml of the cell suspension were vacuum filtered through a pre-weighed Gelman filters (ø47 mm Supor-450, 0.45 µm). Filters were washed with water and dried. Samples for analysis of metabolite concentrations were taken regularly from the reactor. The samples were filtered through 0.2 µm filters. The concentrations of glucose, ethanol and HMF were measured on an Aminex HPX-87H column (Bio-Rad, Hercules, Calif.) at 65° C. The mobile phase was 5 mM $H_2SO_4$ with a flow rate of 0.6 ml/min. All compounds were detected with a refractive index detector, except for HMF which was detected with a UV-detector at 210 nm.

A representative experimental result is shown in FIG. 1. The glucose consumption, ethanol formation and biomass production were similar for both strains when no HMF was added to the medium (FIG. 1A, 1C). On the contrary, when adding HMF to the medium, considerably higher glucose consumption rate, ethanol and biomass production rate were observed in strain TMB3206 overexpressing the mutated ADH1 gene, as compared to the control strain TMB3280 (FIG. 1B, 1D). The experiment confirmed that increased in vitro NADH-dependent HMF reductase activity correlated with increased in vivo HMF reduction rate for strain TMB3206 overexpressing the mutated ADH1 gene.

Anaerobic in vivo HMF Reduction

Inoculum cultures of strains TMB3280 (control) and TMB3206 (overexpressing the mutated ADH1 gene) were grown for 24 hours at 30° C. and 150 rpm in 1 L—shake-flasks with 100 ml of 2 times concentrated defined mineral medium (as described in Verduyn et al., 1992, Effect of benzoic acid on metabolic fluxes in yeasts: a continuous-culture study on the regulation of respiration and alcoholic fermentation. Yeast 8, 501-517) supplemented with 40 g/l glucose and 200 ml/l phtalate buffer (10.2 g/L KH phtalate, 2.2 g/l KOH). The same defined medium, with or without HMF (2 g/l), was used in subsequent batch experiments. The medium was supplemented with 60 g/l glucose, ergosterol (0.075 g/l) and Tween 80 (0.84 g/l). The starting OD620 in batch fermentation was 0.5. Fermentation was carried out in 1 L media at 30° C. in Braun Biotech fermenters. Anaerobic conditions were maintained by continuously sparging 0.2 litre/minute nitrogen gas. pH 5.5 was maintained with 3M KOH. The stirring rate was 200 rpm.

Figure 2:
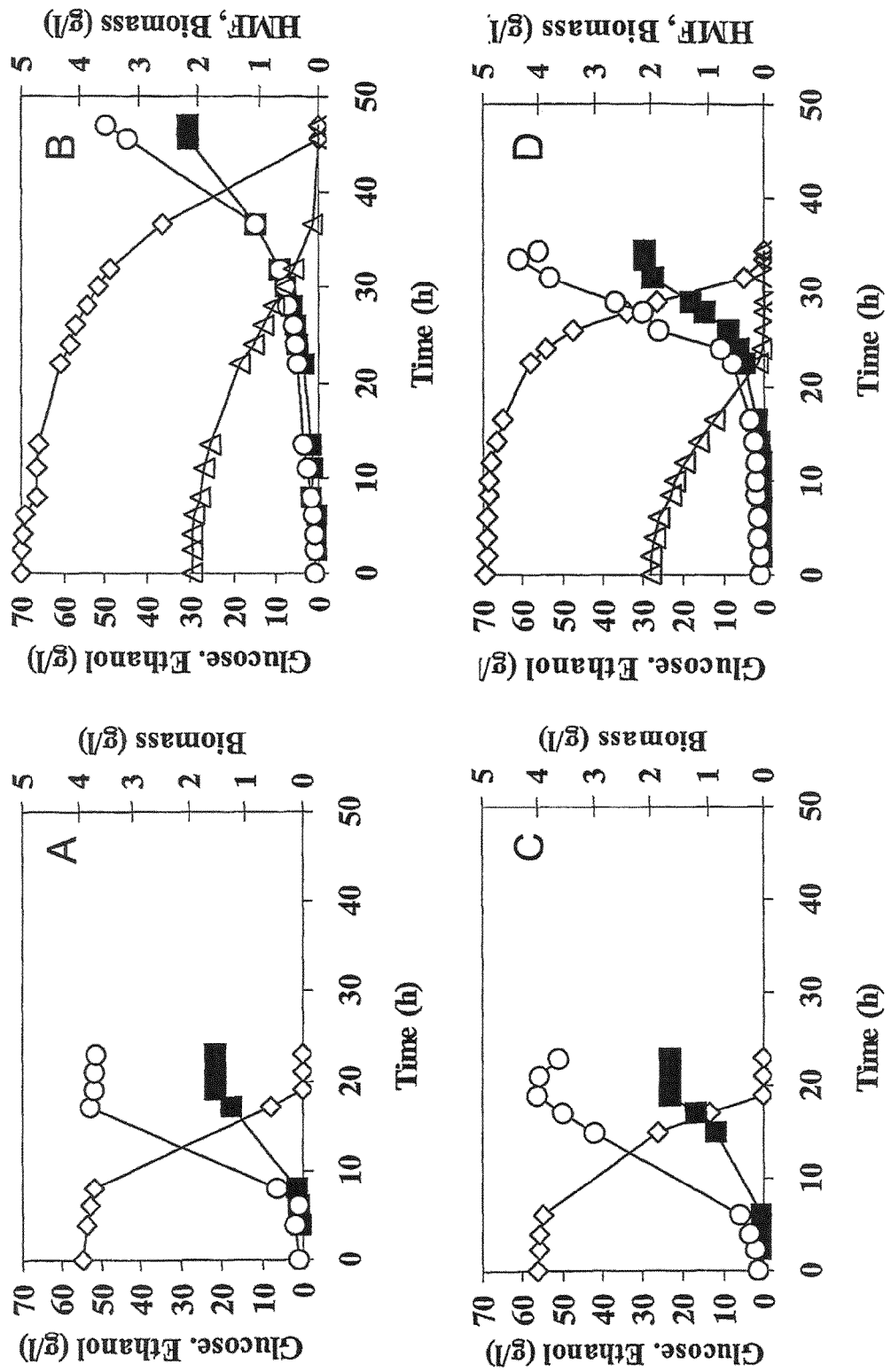
FIG. 2—Substrate and HMF consumption and main product formation in strains TMB3280 (empty plasmid) (A, B) and TMB3206 (mutated ADH1) (C, D) under anaerobic conditions. A, C=without HMF addition; B, D=with 20 mM HMF addition. Symbols: ◇ glucose, ○ $OD_{620}$, Δ HMF, ■ ethanol.

A representative experimental result for the two strains in the presence and absence of HMF is shown in FIG. 2.

Both strains displayed slower growth, glucose conversion and ethanol production when HMF was added to the medium. However, HMF was converted much faster with strain TMB3206 overexpressing mutated ADH1 gene than with the control strain TMB3280. Consequently, glucose consumption started earlier in TMB3206 and full conversion of glucose to ethanol, biomass and other minor products was achieved within 35 hours (FIG. 2D). On the contrary, it took more than 45 hours for the control strain TMB3280 to reach a similar profile (FIG. 2B).

Example 3

Site-directed Mutagenesis on NADH-dependent HMF Reductase

Plasmid YEplacHXT-ADH1-mut encoding the mutated ADH1 gene from TMB3000 (as described in example 1) as well as plasmid YEPlac-HXT encoding the native ADH1 gene from CEN.PK 113-5D (named YEplacHXT-ADH1-nat) were used for site directed mutagenesis in order to investigate the influence of various amino acid mutation on NADH-dependent furan reductase activity.

Site-directed mutagenesis was performed according to the following protocol: A two-step PCR was used for the generation of an ADH1 gene with the chosen amino-acid changes. Six primers were designed for reverse mutagenesis of the mutated ADH1 gene at position 110 (P110S), 117 (S117L) and 295 (C295Y) and four other primers were designed for the mutagenesis of the native ADH1 gene at position 110 (S110P) and 295 (Y295C) (Table 3). Two primers for the amplification of ADH1 gene (mutated or not) were also created: primer ADH1 sense (5'-GGGGGGATCCATGTC-TATCCCAGAAACTC-3'), carrying BamHI site and primer ADH1 antisense (5'-CTTTAGATCTTTATTTAGAAGTGT-CAACAACG-3') carrying BglII site. For reverse mutation of the ADH1 gene from TMB3000, plasmid YEplacHXT-ADH1-mut was used as template. For mutation of the native ADH1 gene, plasmid YEplacHXT-ADH1-nat was used as template.

TABLE 3

Primers used for the site-directed mutagenesis of native and mutated ADH1 gene.

| Primer name | Sequence (5'-3') | Function |
| --- | --- | --- |
| P110S sense | GTGAATTGGGTAACGAATCCAA CTGTCCTCACGC | Reverse mutation at position 110 |
| P110S antisense | GCGTGAGGACAGTTGGATTCGT TACCCAATTCAC | Reverse mutation at position 110 |
| S117L sense | CTGTCCTCACGCTGACTTGTCT GGTTACACCCAC | Reverse mutation at position 117 |
| S117L antisense | GTGGGTGTAACCAGACAAGTCA GCGTGAGGACAG | Reverse mutation at position 117 |
| C295Y sense | CTCCATTGTTGGTTCTTACGTC GGTAACAGAGCTG | Reverse mutation at position 295 |
| C295Y antisense | CAGCTCTGTTACCGACGTAAGA ACCAACAATGGAG | Reverse mutation at position 295 |

TABLE 3-continued

Primers used for the site-directed mutagenesis of native and mutated ADH1 gene.

| Primer name | Sequence (5'-3') | Function |
|---|---|---|
| S110P sense | GGTAACGAACCCAACTGTC | Create mutation at position 110 |
| S110P antisense | GACAGTTGGGTTCGTTACC | Create mutation at position 110 |
| Y295C sense | TTGGTTCTTGCGTCGGTAAC | Create mutation at position 295 |
| Y295C antisense | GTTACCGACGCAAGAACCAA | Create mutation at position 295 |

In the first round of PCR, two fragments were amplified for each targeted mutation: one fragment using primer ADH1 sense and the antisense primer corresponding to the targeted mutation, and another fragment using primer ADH1 antisense and the sense primers corresponding to the targeted mutation. Pwo DNA polymerase (Roche Diagnostics AB, Bromma, Sweden) was used for amplification with the following conditions: initial denaturation at 94° C. for 5 minutes then 30 cycles consisting of a denaturation step at 94° C. for 30 seconds, an annealing step at 55° C. for 30 seconds and an elongation step at 72° C. for 1 minute. The two amplified fragments were purified and used for the second round of PCR, together with primers ADH1 sense and ADH1 antisense, Pwo DNA polymerase and at the following conditions: initial denaturation at 94° C. for 5 minutes then 30 cycles consisting of a denaturation step at 94° C. for 30 seconds, an annealing step at 55° C. for 30 seconds and an elongation step at 72° C. for 1 minute. The amplified fragment was purified and cleaved with BamHI and BglII (Fermentas, Vilnius, Lithuania). The cleaved PCR fragment was ligated to double cleaved YEplacHXT using T4 DNA ligase (Fermentas, Vilnius, Lithuania). The ligation product was used to transform Escherichia coli DH5α cells according to Inoue et al. (1990. High efficiency transformation of Escherichia coli with plasmids. Gene 96:23-28). Transformants were selected on LB medium with 50 μg/ml ampicillin and checked for correct mutation and sequence by restriction analysis and DNA sequencing. Multiple mutations were performed sequentially.

Plasmid carrying individual or combined mutations within the ADH1 gene were introduced in strain CEN.PK 113-5D by transformation according to the lithium acetate method (Gietz et al., 1992, Improved method for high efficiency transformation of intact yeast cells. Nucleic Acids Research 20:1425). Selection was performed on SD plates without uracil. The resulting strains were grown aerobically at 30° C. in 25 mL SD medium without uracil (in 250 mL baffled flask). Cell extracts were prepared by harvesting the cells at $OD_{620}$ 7.5-8.5, re-suspending the cells in Y-PER solution (Pierce, Rockford, Ill., USA), 1 mL/0.6gr cells, shaking at room temperature for 50 min. The supernatant was collected after centrifugation for 20 min at 15000 g. In vitro NADH-dependent furan reductase activity was measured by following the oxidation of NADH at 340 nm in a Hitachi U-2000 spectrophotometer (Hitachi, Tokyo, Japan). The assay consisted of 10 mM furaldehyde (HMF or furfural), 200 μM NADH and cell extract in 100 mM phosphate buffer (pH 6.7) at 30° C. Results are presented in Table 4.

TABLE 4

Mutated amino acids and corresponding NADH-dependent HMF and furfural in vitro activities.

| | | Mutations | | | | NADH-dependent Activity | |
|---|---|---|---|---|---|---|---|
| V59T | Q148E | I152V | S110P | L117S | Y295C | HMF reductase | Furfural Reductase |
| − | − | − | + | − | − | − | ++ |
| − | − | − | − | − | + | + | +++ |
| − | − | − | + | − | + | ++ | ++ |
| + | + | + | − | + | + | + | + |
| + | + | + | + | − | + | ++ | ++ |
| + | + | + | + | + | − | − | + |
| + | + | + | − | − | + | + | +++ |
| + | + | + | + | + | + | + | + |

− no detectable activity,
+ detectable activity (ranging from moderate (+) to very high (+++)).

Example 4

Fermentation of Lignocellulosic Hydrolysate with Strain Overexpressing NADH-dependent HMF Reductase Strains TMB3280 (control) and TMB3206 (overexpressing mutated ADH1 gene from TMB3000) were compared in anaerobic fermentation of undetoxified hydrolysate originating mainly from spruce in a two-stage dilute-kid hydrolysis process using sulphuric acid as the catalyst (Larsson et al. Development of a *Saccharomyces cerevisiae* strain with enhanced resistance to phenolic fermentation inhibitors in lignocellulose hydrolysates by heterologous expression of laccase. *Appl Environ Microbiol* 2001, 67:1163-1170).

Experiments were carried out by adding a single pulse of lignocellulose hydrolysate, previously adjusted to pH 5 with 6 M NaOH, to exponentially growing cells in batch. More specifically, cells were pre-grown in 300 ml shake flasks at 160 rpm and 30° C. for 24 h. The liquid volume in the precultures was 100 ml with a glucose concentration of 15 g/l. Subsequent fermentation was inoculated with 6 ml of the preculture and carried out in Belach BR 0.5 fermentors (Belach Bioteknik AB, Solna, Sweden) at 30° C. and a stirrer speed of 600 rpm. The initial working volume was 300 ml and the pH was kept constant at 5.0 by addition of 0.75 NaOH. The fermentor was continuously sparged with 300 ml/min nitrogen gas (containing less than 5 ppm oxygen) to give anaerobic conditions, controlled by a mass flow meter (Bronkhurst Hi-Tec, Ruurlo, The Netherlands).

Initial concentrations of medium components were 2.67 times higher compared to the inoculum cultures in order to compensate for the dilution. Experiments were started by growing cells on 30 g of glucose in 300 ml growth medium. Next, a single addition of 300 ml of hydrolysate was made when the biomass concentration reached approx. 4 g/l monitored by $OD_{610}$ measurements. The carbon dioxide evolution rate was monitored on-line by measuring the concentrations of carbon dioxide and oxygen in the outgoing gas from the reactor with a CP460 gas analyser (Belach Bioteknik AB, Solna, Sweden). The gas analyzer was calibrated using a gas containing 20% oxygen and 5% carbon dioxide. Cell concentration was determined from absorbance measurements at 610 nm and dry-weight measurements were made from duplicate 10 ml samples, which were centrifuged, washed with distilled water and dried for 24 h at 105° C. Samples for metabolite measurement were immediately centrifuged, filtered through 0.2 µm filters and stored at −20° C. until analysis. The concentrations of glucose, mannose, galactose, HMF and furfural were measured on an Aminex HPX-87P column (Bio-Rad, USA) at 85° C., eluted with ultra-pure water at 0.6 ml/min. The concentrations of ethanol was measured on an Aminex HPX-87H column (Bio-Rad, USA) at 60° C. The eluent used was 5 mM H2SO4 at a flow rate of 0.6 ml/min. Compounds were detected with a refractive index detector, except for HMF and furfural which were detected with a UV-detector (210 nm).

Figure 3:
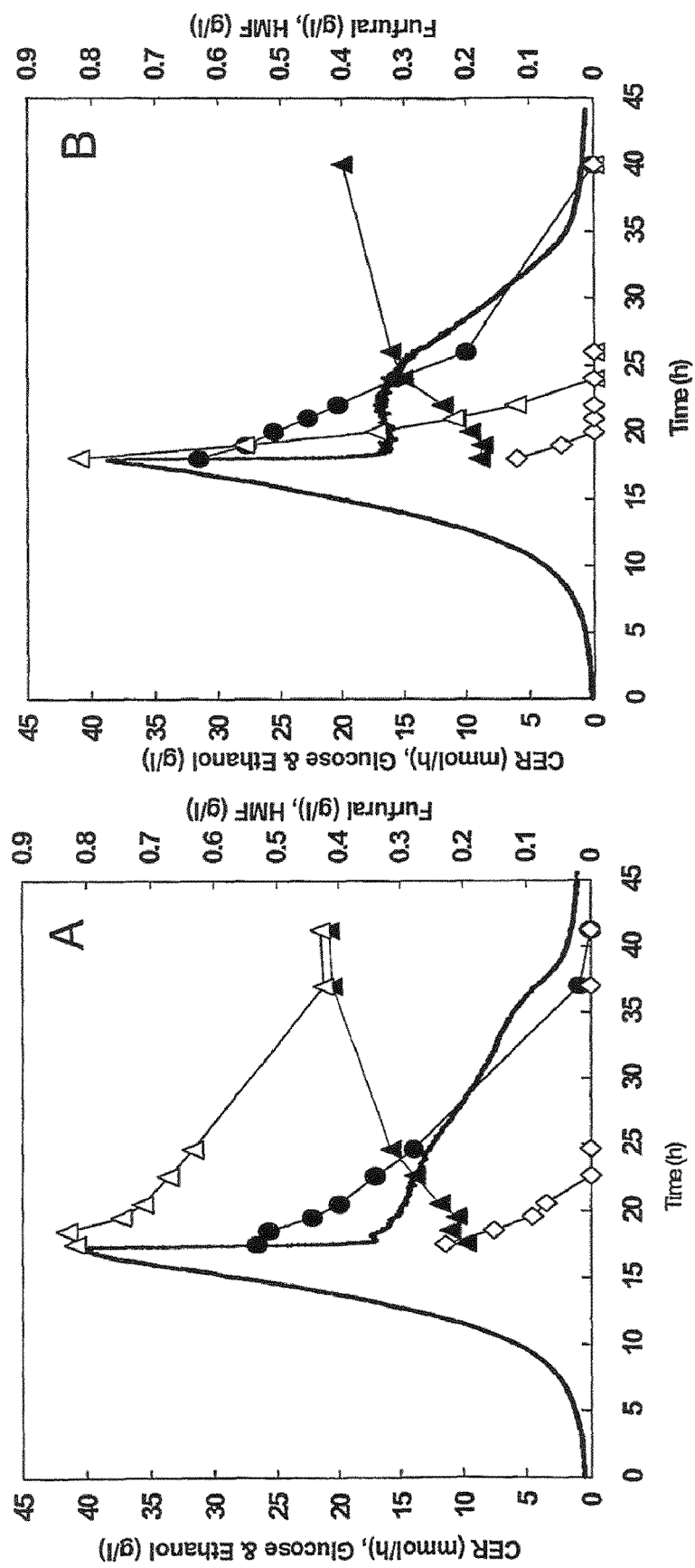
FIG. 3—Fermentation profile of control strain TMB3280 (A) and strain TMB3206 overexpressing the mutated ADH1 gene from TMB3000 (B) in pulse experiment with spruce hydrolysate. Strains are first grown in defined medium, then spruce hydrolysate is added after 15-20 hours. Symbols: Furfural (◇), HMF (Δ), Glucose (●), Ethanol (▲), CO2 evolution rate or CER (-).

Results are presented in FIG. 3. TMB3206 was able to convert furfural and HMF in approximately 5 hours, whereas HMF was still present in the medium 20 hours after hydrolysate addition in the experiment with the control strain TMB3280. TMB3206, which had 5 times higher HMF uptake rate, showed a more or less constant CER (FIG. 3B), while CER gradually decreased for the control strain (FIG. 3A). The specific ethanol productivity was also lower for the control strain compared with TMB3206 overexpressing the mutated ADH1 gene.

Example 5

Changing Cofactor Balance and Product Formation in a Strain Expressing NADH-dependent HMF Reductase and the *Pichia stipitis* Xylose Pathway Overexpression in *S. cerevisiae* TMB3320

Plasmid YEplac-HXT-ADH1-S110P-Y295C encoding a mutated ADH1 gene (as described in Table 4), as well as the corresponding empty plasmid YEplacHXT (Karhumaa et al., 2005, Investigation of limiting metabolic steps in the utilization of xylose by recombinant *Saccharomyces cerevisiae* using metabolic engineering. Yeast. 22(5):359-368) were used to transform the xylose consuming strain *S. cerevisiae* TMB3320 resulting in strains TMB3291 and TMB3290, respectively. TMB3320 was obtained by transformation of TMB3043 (leu2, ura3) with the plasmid YIplac128-XRXDH, which directs the expression of xylose reductase and xylitol dehydrogenase from *Pichia stipitis*. As expected, NADH-dependent HMF reductase activity was only detected in the strain carrying the mutated ADH1 gene (data not shown).

Changes in Cofactor Balance in Anaerobic Continuous Culture with HMF

Strains TMB3291 and TMB3290 were pre-grown overnight at 30° C. and 200 rpm in 1 L—shake-flasks with 100 ml defined medium (Verduyn et al., 1992. Effect of benzoic acid on metabolic fluxes in yeasts: a continuous-culture study on the regulation of respiration and alcoholic fermentation. Yeast, 8, 501-517) supplemented with 20 g/l glucose. The same defined medium supplemented with ergosterol (0.075 g/l) and Tween 80 (0.84 g/l), with or without HMF (2 g/l), was used in subsequent continuous culture experiments. The starting OD620 in the fermentor was 0.2. Fermentation was carried out in 400 mL media at 30° C. in Belach Biotech fermentors with dilution rates of 0.06 $h^{-1}$ and 0.12 $h^{-1}$. Anaerobic conditions were maintained by continuously sparging 0.2 litre/minute nitrogen gas. The stirring rate was 600 rpm and pH 5.5 was maintained with 0.75M NaOH.

Cell concentration was determined from dry-weight measurements from duplicate samples. For dry-weight samples 5 ml of the cell suspension were vacuum filtered through pre-weighed Gelman filters (ø47 mm Supor-450, 0.45 µm). Filters were washed with water and dried. Samples for analysis of metabolite concentrations were taken at culture steady-state, i.e. carbon dioxide production was constant after approximately 5 culture volume changes. The samples were filtered through 0.2 µm filters. The concentrations of glucose, xylose, xylitol, glycerol, acetate, ethanol and HMF were separated on an Aminex HPX-87H column (Bio-Rad, Hercules, Calif.) at 65° C. The mobile phase was 5 mM $H_2SO_4$ with a flow rate of 0.6 ml/min. All compounds were detected with a refractive index detector, except for HMF which was detected with a UV-detector at 210 nm.

The glucose and xylose consumption and product formation were similar for both strains when no HMF was added to the feed-medium. In contrast, when adding HMF to the feed-medium, considerably changes occurred. The xylitol yield decreased for the strain TMB3291 (ADH1-S110P-Y295C) while it increased for TMB3290 strain (control). The glycerol yields were 50% less for the ADH1-S110P-Y295C strain, while it was not affected in the control strain. Furthermore, biomass yields of ADH1-S110P-Y295C strain increased in presence of HMF. Acetate yields increased for both strains. With the highest dilution rate (0.12 $h^{-1}$) xylose consumption decreased 50% for control strain but was not affect in ADH1-S110P-Y295C strain. Furthermore, half of the added HMF in the feed was still present in the fermentor with control strain, but it was completely converted in the fermentor with ADH1-S110P-Y295C strain. Ethanol yields for both strains were not affected by the addition of HMF and were the same for both strains.

The experiment confirmed that increased in vivo NADH-dependent HMF reduction changes cofactor balance and consequently by-product distribution in *S. cerevisiae* strains.

Example 6

Improved Ethanol Production in a Strain Expressing NADH-dependent HMF Reductase and the *Pichia stipitis* Xylose Pathway Anaerobic in vivo HMF Reduction Inoculum cultures of strains TMB3290 (control) and TMB3291 (overexpressing the mutated ADM-S110P-Y295C gene) were grown overnight at 30° C. and 150 rpm in 1 L—shake-flasks with 100 ml of 2 times concentrated defined mineral medium (as described in Verduyn et al., 1992, Effect of benzoic acid on metabolic fluxes in yeasts: a continuous-culture study on the regulation of respiration and alcoholic fermentation. Yeast 8, 501-517) supplemented with 40 g/l glucose and 200 ml/l phtalate buffer (10.2 g/L KH phtalate, 2.2 g/l KOH). The same defined medium with or without HMF (2 g/l), was used in subsequent batch experiments. The medium was supplemented with 20 g/l glucose, 50 g/l xylose, ergosterol (0.075 g/l) and Tween 80 (0.84 g/l). The starting OD620 in batch fermentation was 0.5. Fermentation was carried out in 1 L media at 30° C. in Braun Biotech fermentors. pH 5.5 was maintained with 3M KOH. The stirring rate was 200 rpm.

Figure 4:
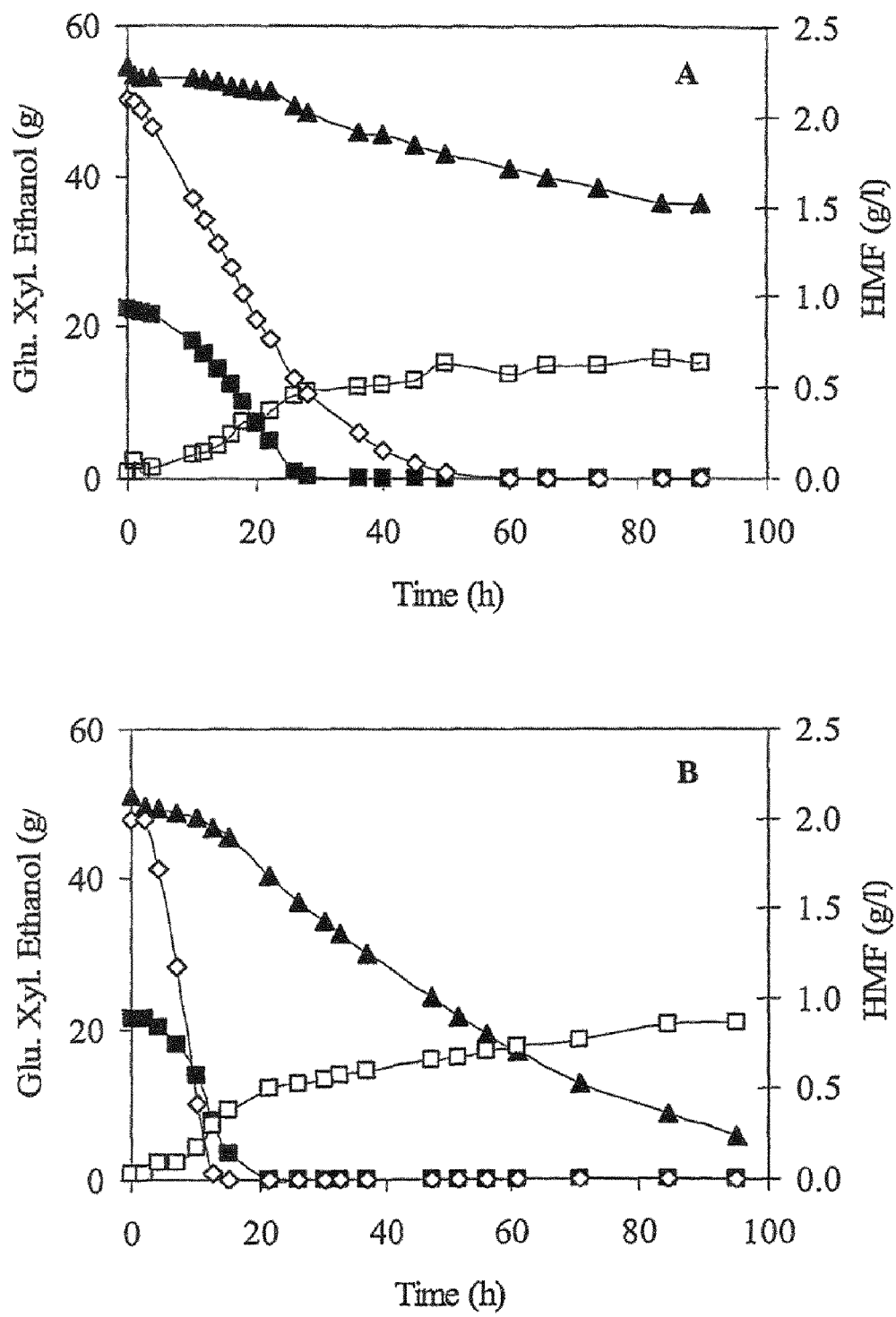
FIG. 4—Substrate and HMF consumption and ethanol formation in strains TMB3290 (empty plasmid) (A) and TMB3291 (ADH1-S110P-Y295C) (B) under anaerobic conditions. Symbols: (■) glucose, (▲) xylose, (◇) HMF, (□) ethanol.

A representative experimental result for the two strains in the presence and absence of HMF is shown in FIG. 4.

The glucose and xylose consumption and product formation were similar for both strains when no HMF was added to the medium (data not shown). In presence of HMF, the control strain (TMB3290) consumed glucose and xylose slower than the ADH1-S110P-Y295C strain (TMB3291)(FIG. 4). Furthermore, at the end of the fermentation the ADH1-S110P-

Y295C strain had consumed twice as much xylose as the control strain, which resulted in higher final ethanol concentration. The results support that the HMF conversion is faster in ADH1-S110P-Y295C strain (FIG. 4).

Example 7

Kinetic Characterization of ADH1 Mutants

Plasmids carrying individual or combined mutations within the ADH1 gene generated by site directed mutagenesis in Example 3 were introduced in strain BY4741 by transformation according to the lithium acetate method (Gietz et al., 1992, Improved method for high efficiency transformation of intact yeast cells. Nucleic Acids Research 20:1425). Selection was performed on SD plates without uracil. The resulting strains and the corresponding mutations are summarized in Table 5.

Cells were grown aerobically at 30° C. in 25 mL SD medium without uracil (in 250 mL baffled flask). Cell extracts were prepared by harvesting the cells at OD620 7.5-8.5, resuspending the cells in Y-PER solution (Pierce, Rockford, Ill., USA), 1 mL/0.6 gr cells, shaking at room temperature for 50 min. The supernatant was collected after centrifugation for 20 min at 15000 g.

In vitro NADH-dependent furan reductase activity was measured by following the oxidation of NADH at 340 nm in a Hitachi U-2000 spectrophotometer (Hitachi, Tokyo, Japan). NADH-dependent aldehyde reduction was determined (Wahlbom and Hahn-Hägerdal, 2002) with 200 μM NADH. Reduction kinetics were determined for acetaldehyde (range 500W-100 mM), furfural (100 μM-20 mM) and HMF (500 μM-20 mM). For native Adh1 furfural was used up to 40 mM.

Modeling was performed according to the Michaelis-Menten equation with the addition of a substrate inhibition constant: $V=(V_{max} \cdot [S])/(K_m+[S]+[S]^2/K_I)$, V—velocity, Vmax—maximal velocity, Km—affinity constant, Ki—substrate inhibition constant, and [S]—substrate concentration.

Parameter value estimation was according to the least square method, using the solver function in Microsoft® Excel 2002. HMF activity parameters of strain BY474-ADH1-S117L were estimated without the substrate inhibition constant due to a clear discrepancy of the substrate inhibition model with actual data.

The results are summarized in table 6. The improved values for Km and Vmax of the different mutants clearly demonstrated the importance of mutation Y295C for HMF and furfural reduction. Comparison of kinetic parameters of the strains BY474-ADH1-S117L and BY4741-ADH1-110P-L117S-295C showed that L in position 117 is beneficial, since it significantly increases activities towards both furaldehydes.

TABLE 5

Strains and amino-acid differences among different Adh1 variants

| Strain | Position | | | | | |
|---|---|---|---|---|---|---|
| Position | 59 | 110 | 117 | 148 | 152 | 295 |
| BY4741-control | V | S | L | Q | I | Y |
| BY4741-ADH1-S110P-Y295C | V | P | L | Q | I | C |
| BY4741-ADH1-Y295C | T | S | L | E | V | C |
| BY474-ADH1-S117L | T | P | L | E | V | C |
| BY4741-ADH1-110P-L117S-295C | T | P | S | E | V | C |

TABLE 6

Enzyme kinetics of five Adh1 variants against different substrates. Kinetic parameters were established with cell extracts of ΔAdh1 strain (BY4741) with the respective ORF overexpressed.

| Adh1 variant | BY4741-control | BY4741-ADH1-S109P-Y294C | BY4741-ADH1-Y294C | BY474-ADH1-S116L | BY4741-ADH1-109P-L116S-294C |
|---|---|---|---|---|---|
| HMF | | | | | |
| Vmax (mU)/mg | n.d | 11090 | 3640 | 6320** | 3120 |
| Km (mM) | | 9.45 | 13.1 | 4.28 | 4.3 |
| Ki (mM) | | 20.8 | 27.3 | n.d | 9.82 |
| $[S]_{Vmax}$, $(obsV_{max})$* | | 10-20 (4560) | 20 (1550) | 10 (4900) | 5-10 (1320) |
| RSQ | | 0.999 | 0.98 | 0.975 | 0.984 |
| Furfural | | | | | |
| Vmax (mU)/mg | 6530 | 5657 | 7792 | 11700 | 1625 |
| Km (mM) | 18.8 | 0.13 | 0.34 | 0.33 | 0.04 |
| Ki (mM) | 1363 | 1.32 | 6.66 | 4.4 | 1.07 |
| $[S]_{Vmax}$, $(obsV_{max})$* | 30 (4345) | 0.25-0.5 (3480) | 1 (5320) | 1 (7600) | 0.25 (1230) |

TABLE 6-continued

Enzyme kinetics of five Adh1 variants against different substrates. Kinetic parameters were established with cell extracts of ΔAdh1 strain (BY4741) with the respective ORF overexpressed.

| Adh1 variant | BY4741-control | BY4741-ADH1-S109P-Y294C | BY4741-ADH1-Y294C | BY474-ADH1-S116L | BY4741-ADH1-109P-L116S-294C |
|---|---|---|---|---|---|
| RSQ | 0.97 | 0.984 | 0.986 | 0.992 | 0.974 |
| | | | Acetaldehyde | | |
| Vmax (mU)/mg | 45070 | 16509 | 32455 | 23060 | 4736 |
| Km (mM) | 0.216899 | 0.83 | 3.03 | 1.74 | 1.69 |
| Ki (mM) | 12.5326 | 46 | 56 | 96 | 49 |
| $[S]_{Vmax}$, $(obsV_{max})$* | 1 (35300) | 5 (14300) | 10 (22000) | 10-25 (17600) | 10 (3700) |
| RSQ | 0.987 | 0.97 | 0.974 | 0.979 | 0.968 |

*$[S]_{Vmax}$ - substrate concentration (mM) at observed $V_{max}$ ($obsV_{max}$, mU/mg)
**$V_{max}$ and $K_m$ values derived from a model without substrate inhibition factor, see text for details
n.d. - not detected

The invention claimed is:

1. An isolated polypeptide having NADH dependent HMF reductase activity, wherein said polypeptide shows 90% homology to the amino acid sequence shown in SEQ ID NO:2 and which differs from SEQ ID NO:2 by comprising S117L and also comprising Y295C, Y295S, Y295T or S110P.

2. The isolated polypeptide according to any of claim 1, wherein said polypeptide differs from SEQ ID NO:2 in that S 117L and Y295C and S110P are substituted.

3. The isolated polypeptide according to claim 1, wherein said polypeptide has at least 95% homology to SEQ ID NO:2.

4. The isolated polypeptide according to claim 3, wherein said polypeptide has at least 98% homology to SEQ ID NO:2.

5. The isolated polypeptide according to claim 4, wherein said polypeptide has at least 98.5% homology to SEQ ID NO:2.

6. The isolated polypeptide according to claim 5, wherein said polypeptide has at least 98.7% homology to SEQ ID NO:2.

7. The isolated polypeptide according to claim 6, wherein said polypeptide has at least 98.8% homology to SEQ ID NO:2.

8. The isolated polypeptide according to claim 7, wherein said polypeptide has at least 99% homology to SEQ ID NO:2.

9. An isolated nucleotide sequence encoding the polypeptide according to claim 1.

10. A vector comprising a nucleotide sequence as defined in claim 9.

11. A host cell comprising a nucleotide sequence as defined in claim 10 or a vector as defined in claim 10.

12. The host cell according to claim 11, wherein said host cell is selected from the group consisting of eukaryotic and prokaryotic cells.

13. The host cell according to claim 12, wherein said cells are selected from the group consisting of bacteria, yeast and fungi.

14. The host cell according to claim 13, wherein said bacteria is selected from the group consisting of *Escherichia coli*, *Klebsiella* sp. and *Zymomonas mobilis* and said fungi is filamentous fungi.

15. The host cell according to claim 13, wherein said yeast cell is selected from the group *Saccharomyces* sp., *Schizosaccharomyces* sp., *Kluyveromyces* sp., *Pichia* sp., *Hansenula* sp., *Candida* sp., and *Yarrowia* sp.

16. The host cell according to claim 15 wherein said host cell is selected from the group consisting of *Saccharomyces cerevisiae, Saccharomyces bay anus* and *Saccharomyces carlsbergensis*.

17. The host cell according to claim 16 wherein said host cell is *Saccharomyces cerevisiae*.

* * * * *

UNITED STATES PATENT AND TRADEMARK OFFICE
CERTIFICATE OF CORRECTION

| | | |
|---|---|---|
| PATENT NO. | : 8,110,387 B2 | |
| APPLICATION NO. | : 12/671241 | |
| DATED | : February 7, 2012 | |
| INVENTOR(S) | : Hahnhagerdal et al. | |

It is certified that error appears in the above-identified patent and that said Letters Patent is hereby corrected as shown below:

Title page, (73) Assignee: "C5 Ligno Technologies Lund AB" should read --C5 Ligno Technologies in Lund AB--

Signed and Sealed this
Third Day of July, 2012

David J. Kappos
*Director of the United States Patent and Trademark Office*